US012636439B2

(12) United States Patent
Moeller

(10) Patent No.: US 12,636,439 B2
(45) Date of Patent: May 26, 2026

(54) DOSE DELIVERY DEVICE WITH GEARING

(71) Applicant: Shaily (UK) Ltd, Croydon (GB)

(72) Inventor: Claus Schmidt Moeller, Fredensborg (DK)

(73) Assignee: SHAILY INNOVATIONS LTD, Croydon (GB)

( * ) Notice: Subject to any disclaimer, the term of this patent is extended or adjusted under 35 U.S.C. 154(b) by 321 days.

(21) Appl. No.: 18/008,658

(22) PCT Filed: Jan. 21, 2022

(86) PCT No.: PCT/GB2022/050163
§ 371 (c)(1),
(2) Date: Dec. 6, 2022

(87) PCT Pub. No.: WO2022/171976
PCT Pub. Date: Aug. 18, 2022

(65) Prior Publication Data
US 2023/0372628 A1      Nov. 23, 2023

(30) Foreign Application Priority Data

Feb. 9, 2021     (GB) ..................................... 2101765

(51) Int. Cl.
*A61M 5/315*         (2006.01)
(52) U.S. Cl.
CPC .... *A61M 5/31551* (2013.01); *A61M 5/31558* (2013.01); *A61M 5/31561* (2013.01);
(Continued)
(58) Field of Classification Search
CPC .......... A61M 5/31551; A61M 5/31558; A61M 5/31561; A61M 5/3158; A61M 5/31593;
(Continued)

(56) References Cited

U.S. PATENT DOCUMENTS

| 6,221,046 B1 | 4/2001 | Burroughs et al. |
| 6,235,004 B1 | 5/2001 | Steenfeldt-Jensen et al. |

(Continued)

FOREIGN PATENT DOCUMENTS

| CN | 103189084 A | 7/2013 |
| WO | 2005018721 A1 | 3/2005 |

OTHER PUBLICATIONS

The Intellectual Property Office Search Report Under section 17 for Application No. GB 2101765.2, dated Jul. 12, 2021.

(Continued)

*Primary Examiner* — Laura A Bouchelle
*Assistant Examiner* — Sarah Dympna Grasmeder
(74) *Attorney, Agent, or Firm* — Kilyk & Bowersox, P.L.L.C.

(57) ABSTRACT

In a dose setting mode of a dose delivery device, a dose selector is rotated to turn a nut, which thereby moves backward along a thread of a piston rod through a first axial distance. A gearing mechanism transmits the axial movement of the nut to a connector that moves backward, without rotation, through a second axial distance. In a dose delivery mode of the device, the dose selector is pushed forward and drives the connector to move forward through the second axial distance. The gearing mechanism transmits the axial movement of the connector to the nut, which pushes the piston rod forward, without rotation, through the first axial distance. The gearing mechanism includes a first gear that rotates without axial movement relative to the housing, and a second gear that rotates without axial movement relative to the nut.

14 Claims, 10 Drawing Sheets

(52) U.S. Cl.
CPC ...... *A61M 5/3158* (2013.01); *A61M 5/31593* (2013.01); *A61M 2205/581* (2013.01); *A61M 2205/582* (2013.01)

(58) Field of Classification Search
CPC ...... A61M 2205/581; A61M 2205/582; A61M 5/31575; A61M 5/31528
See application file for complete search history.

(56) References Cited

U.S. PATENT DOCUMENTS

| | | | |
|---|---|---|---|
| 7,850,662 B2 | 12/2010 | Veasey et al. | |
| 7,918,833 B2 | 4/2011 | Veasey et al. | |
| 7,935,088 B2 | 5/2011 | Veasey et al. | |
| 8,512,297 B2 | 8/2013 | Veasey et al. | |
| 8,556,864 B2 | 10/2013 | Veasey et al. | |
| 8,603,044 B2 | 12/2013 | Veasey et al. | |
| 8,679,069 B2 | 3/2014 | Veasey et al. | |
| 8,864,721 B2 | 10/2014 | Moller | |
| 8,992,486 B2 | 3/2015 | Veasey et al. | |
| 9,011,391 B2 | 4/2015 | Veasey et al. | |
| 9,028,454 B2 | 5/2015 | Veasey et al. | |
| 9,233,211 B2 | 1/2016 | Veasey et al. | |
| 9,408,979 B2 | 8/2016 | Veasey et al. | |
| 9,526,844 B2 | 12/2016 | Veasey et al. | |
| 9,533,105 B2 | 1/2017 | Veasey et al. | |
| 9,561,331 B2 | 2/2017 | Veasey et al. | |
| 9,604,008 B2 | 3/2017 | Veasey et al. | |
| 9,604,009 B2 | 3/2017 | Veasey et al. | |
| 9,610,409 B2 | 4/2017 | Veasey et al. | |
| 9,623,189 B2 | 4/2017 | Veasey et al. | |
| 9,623,190 B2 | 4/2017 | Veasey et al. | |
| 9,775,954 B2 | 10/2017 | Veasey et al. | |
| 9,827,379 B2 | 11/2017 | Veasey et al. | |
| 10,653,841 B2 | 5/2020 | Veasey et al. | |
| 10,729,855 B2 | 8/2020 | Veasey et al. | |
| 2004/0267208 A1 | 12/2004 | Veasey et al. | |
| 2005/0033244 A1 | 2/2005 | Veasey et al. | |
| 2008/0027397 A1 | 1/2008 | Deruntz et al. | |
| 2015/0038916 A1* | 2/2015 | Moller | A61M 5/31525 604/211 |
| 2017/0340832 A1 | 11/2017 | Veasey et al. | |
| 2019/0117898 A1 | 4/2019 | Hirschel et al. | |
| 2019/0240412 A1 | 8/2019 | Veasey et al. | |
| 2020/0238011 A1 | 7/2020 | Veasey et al. | |

OTHER PUBLICATIONS

International Search Report for Application No. PCT/GB2022/050613, from the European Patent Office as ISA, dated May 3, 2022.
Written Opinion of the International Search Authority, for Application No. PCT/GB2022/050613, from the European Patent Office as ISA, dated May 3, 2022.

\* cited by examiner

DOSE DELIVERY DEVICE WITH GEARING

TECHNICAL FIELD

The invention relates to dose delivery devices, also referred to as injector pens, which provide a mechanism for setting a dose of a drug then delivering that dose to a patient from a drug cartridge. The dose is typically set by moving a dose selector to a position that corresponds to the desired dose, then the dose is delivered by pushing the dose selector through a first distance back to its initial position. The drug cartridge typically contains multiple doses of the drug in a chamber and the dose delivery device comprises a piston rod that is advanced to expel each dose from the chamber, the piston rod moving through a second distance that determines the volume of the dose delivered. The invention relates in particular to geared dose delivery devices, in which the first distance is not equal to the second distance.

BACKGROUND OF THE INVENTION

Geared dose delivery devices are known. Because the volume of drug to be delivered from the cartridge is often quite small, the piston rod needs to advance through only a small axial distance to deliver a typical dose. Gearing provides a first benefit that the push button and/or dose selector can be arranged to move through a larger distance, which is typically proportional to the distance moved by the piston rod. This allows the user to set the desired dose more precisely. Gearing also provides a second benefit resulting from an improved mechanical advantage of the mechanism. In many situations, enabling the user to apply a small force over a longer distance rather than a large force over a shorter distance makes drug delivery easier and more controlled. It is necessary to ensure that this benefit is not outweighed by the additional friction that the gearing mechanism introduces.

In some dose delivery devices, the movement of the dose selector in the drug delivery mode is driven automatically by the energy of a spring, instead of manually by pressure applied by the user. The user adds energy to the spring as the dose selector is moved during the dose setting mode. The benefits of gearing also apply to such automatic devices, which are not excluded from the scope of the present invention.

SUMMARY OF THE INVENTION

The invention provides a dose delivery device, as defined in claim 1.

The invention further provides a method of operating a dose delivery device, as defined in claim 9.

Preferred but non-essential features of the invention are defined in the dependent claims.

In this specification, the word "drug" is used to describe any fluid substance that is to be delivered by the pen in measured doses. It will typically be a biologically active substance that is injected into the body of a human or animal subject, e.g. for medicinal or cosmetic purposes. However, the invention could be used in other applications where it is desired to dispense fixed quantities of a substance.

In this specification, terms such as "front" and "forwards" indicate the direction towards the end of the drug delivery device where the needle is located, which is shown at the bottom of the drawings. Terms such as "rear" and "backwards" indicate the opposite direction.

THE DRAWINGS

DETAILED DESCRIPTION

Figure 1:
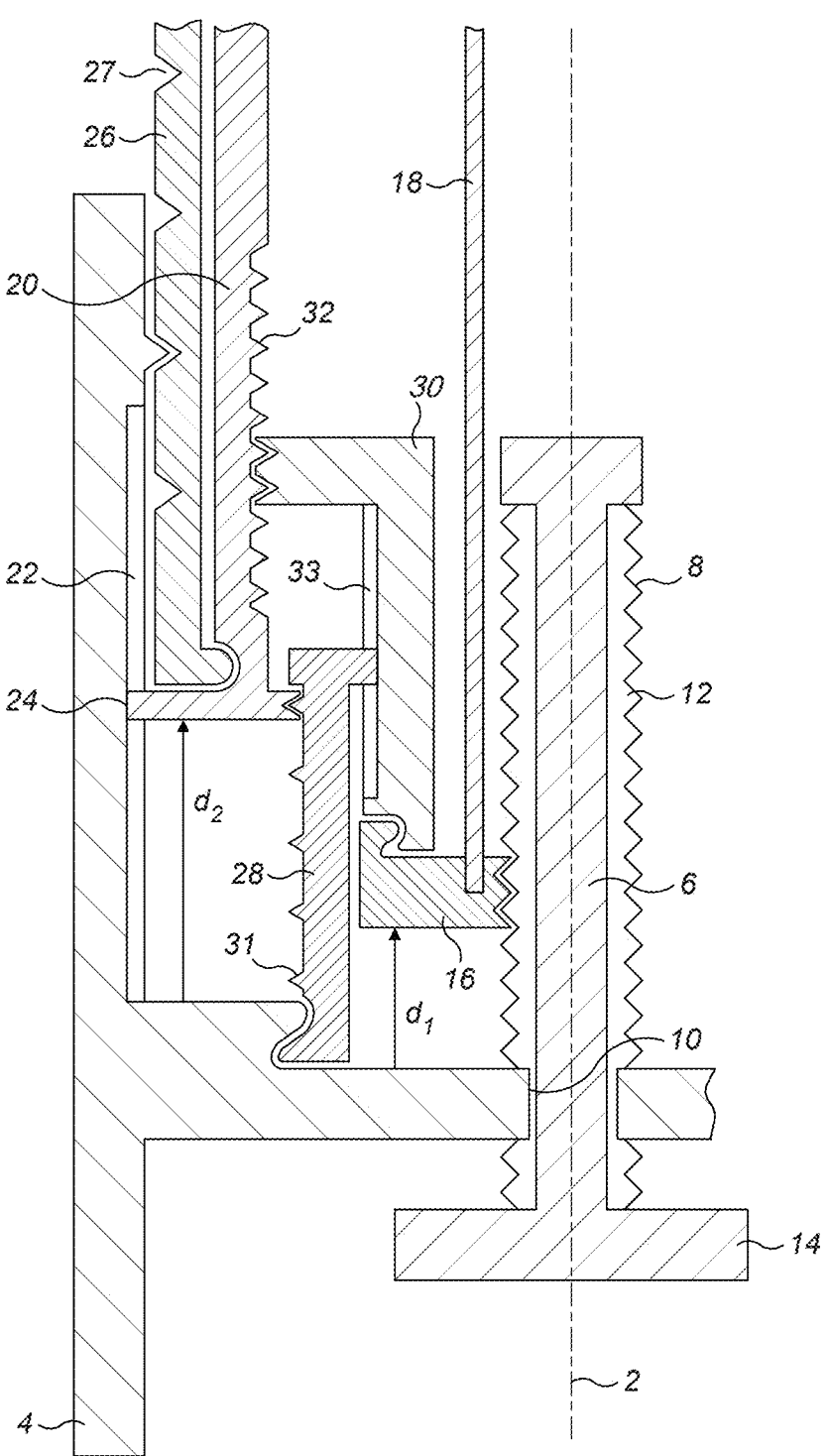
FIG. 1 is a schematic illustration of a first gearing mechanism in accordance with the present invention.

FIG. 1 is a highly schematic illustration, in cross section, of the gearing mechanism of a dose delivery device. In particular, the dimensions perpendicular to the axis 2 have been exaggerated to introduce space and promote clarity. The mechanism is illustrated on substantially only one side of the axis 2. The other side is a mirror image except for the handedness of the threads.

A generally cylindrical housing 4 surrounds the axis 2 and contains the gearing mechanism. A piston rod 6 aligned with the axis 2 comprises a piston rod thread 8 on its outer surface. The piston rod 6 is configured to slide without rotation through a central aperture 10 that is fixed relative to the housing 4. The piston rod thread 8 is interrupted by a pair of opposing flats or by two or more longitudinal tracks 12, thereby providing the piston rod 6 with a non-circular cross section that complements the shape of the aperture 10 and prevents the piston rod 6 from rotating relative to the housing 4. At a front end of the piston rod 6, beyond the aperture 10 and remote from the gearing mechanism, a foot 14 is configured to engage the piston of a drug cartridge (not illustrated) that may be attached to the device. A front end of the drug cartridge may be pierced by a hollow needle (not illustrated), whereby forward movement of the piston rod 6 along the axis 2 causes the piston to advance along the drug cartridge and expel a measured quantity of drug from the cartridge through the needle.

A nut 16 comprises an internal thread, by which it engages the piston rod thread 8 so that rotation of the nut 16 causes it to travel along the thread 8. A rigid tube 18 surrounds the piston rod 6 and extends rearwards from the nut 16. The tube 18 is fixed to the nut 16 so that it follows the movement of the nut.

A generally cylindrical connector 20 surrounds the axis 2 and is configured to move axially without rotation relative to the housing 4. Internal walls of the housing 4 may be provided with one or more axial tracks 22 and the connector 20 may comprise a corresponding number of radially projecting lugs 24 that slide in the respective tracks 22.

A generally cylindrical dose dial sleeve 26 is concentric with the axis 2 and is nested radially between the housing 4 and the connector 20. It engages the connector 20 in such a way that the dose dial sleeve 26 is constrained to move axially with the connector 20 but relative rotation between them is permitted. The dose dial sleeve 26 engages the housing via a sleeve thread 27 so that any axial movement of the dose dial sleeve 26 relative to the housing 4 must be accompanied by simultaneous rotation of the dose dial sleeve 26 along the sleeve thread 27. The sleeve thread 27 has the same handedness as the piston rod thread 8 but a greater pitch.

We now describe the operation of the gearing mechanism; more detail of other parts of the device will be provided below in relation to the specific embodiment illustrated in FIGS. 3 to 6 below.

During a dose setting mode of operation, the tube 18 is rotated and causes the nut 16 to move backwards, following the piston rod thread 8, through a first axial distance $d_1$, which corresponds to the dose of drug to be delivered. At the same time, the connector 20 moves axially backwards, without rotation, through a second axial distance $d_2$ that is greater than the first axial distance $d_1$, thereby providing the aforementioned benefits of a geared dose delivery device. In the example illustrated in FIG. 1, the second axial distance $d_2$ is twice as great as the first axial distance $d_1$ but in other examples the gear ratio may be larger or smaller. During a dose delivery mode of operation, the connector 20 is pushed forwards to return to its initial position. The nut 16 simultaneously moves forwards through the first axial distance $d_1$, this time without rotation, to return to its initial axial position but not necessarily to its initial rotational position. This forward movement of the nut 16 advances the piston rod 6 through the first axial distance $d_1$, thereby displacing a proportionate dose of the drug from the drug cartridge.

The differential movement between the nut 16 and the connector 20 is mediated by a first gear 28 and a second gear 30. The first and second gears 28,30 are generally cylindrical and are concentric with the axis 2, being nested between the tube 18 and the connector 20. The first gear 28 is coupled to the housing 4 such that, relative to the housing 4, it is prevented from moving axially but is free to rotate. The first gear 28 is coupled to the connector 20 by a first engagement in the form of a first helical thread 31. The second gear 30 is coupled to the nut 16 so as to permit relative rotation but not relative axial movement between the second gear 30 and the nut 16. The second gear 30 is coupled to the connector 20 by a second engagement 32 and to the first gear by a third engagement 33.

In the gearing mechanism illustrated in FIG. 1, the third engagement 33 between the first and second gears 28,30 is a straight track, which permits relative axial movement but prevents relative rotation between the gears. The second engagement, between the second gear 30 and the connector 20, is a second helical thread 32 having the same handedness as the first helical thread 31 but a smaller pitch. The handedness of the first and second helical threads 31,32 may be the same as or opposite to the handedness of the piston rod thread 8 and the sleeve thread 27.

During operation of the device, the first gear 28 is prevented from moving axially, the second gear 30 moves axially with the nut 16 through the first axial distance $d_1$ and the connector 20 moves axially through the second axial distance $d_2$. The connector 20 engages the first gear 28 via the first helical thread 31 so the axial movement of the connector 20 relative to the first gear 28 causes the first gear 28 to rotate at a rate determined by the pitch of the first helical thread 31. Because the first and second gears 28,30 are coupled by a straight track 33, the second gear 30 co-rotates with the first gear 28, while the straight track 33 accommodates the relative axial movement between the first and second gears 28,30. Relative to the connector 20, the second gear 30 rotates at a rate determined by the first gear 28 and moves axially at a rate determined by the difference between $d_1$ and $d_2$. The pitch of the second helical thread 32 must therefore be such that it can accommodate these simultaneous relative axial and rotational movements. In practice, the values are related by the following equation:

$$\frac{p_2}{p_1} = 1 - \frac{1}{R}$$

where:

$p_1$ is the pitch of the first helical thread 31, $p_2$ is the pitch of the second helical thread 32, and R is the gear ratio, $R=d_2/d_1$ The gear ratio R is also equal to the ratio between the pitch of the sleeve thread 27 and the pitch of the piston rod thread 8.

The pitches $p_1$ and $p_2$ of the first and second helical threads 31,32 may be chosen to have any suitable values, provided they are in this ratio. In particular, both threads may have a high pitch in order that they should offer low frictional resistance when force is applied to the gearing mechanism to drive the axial movement of the nut 16 during the dose delivery mode.

Figure 2:
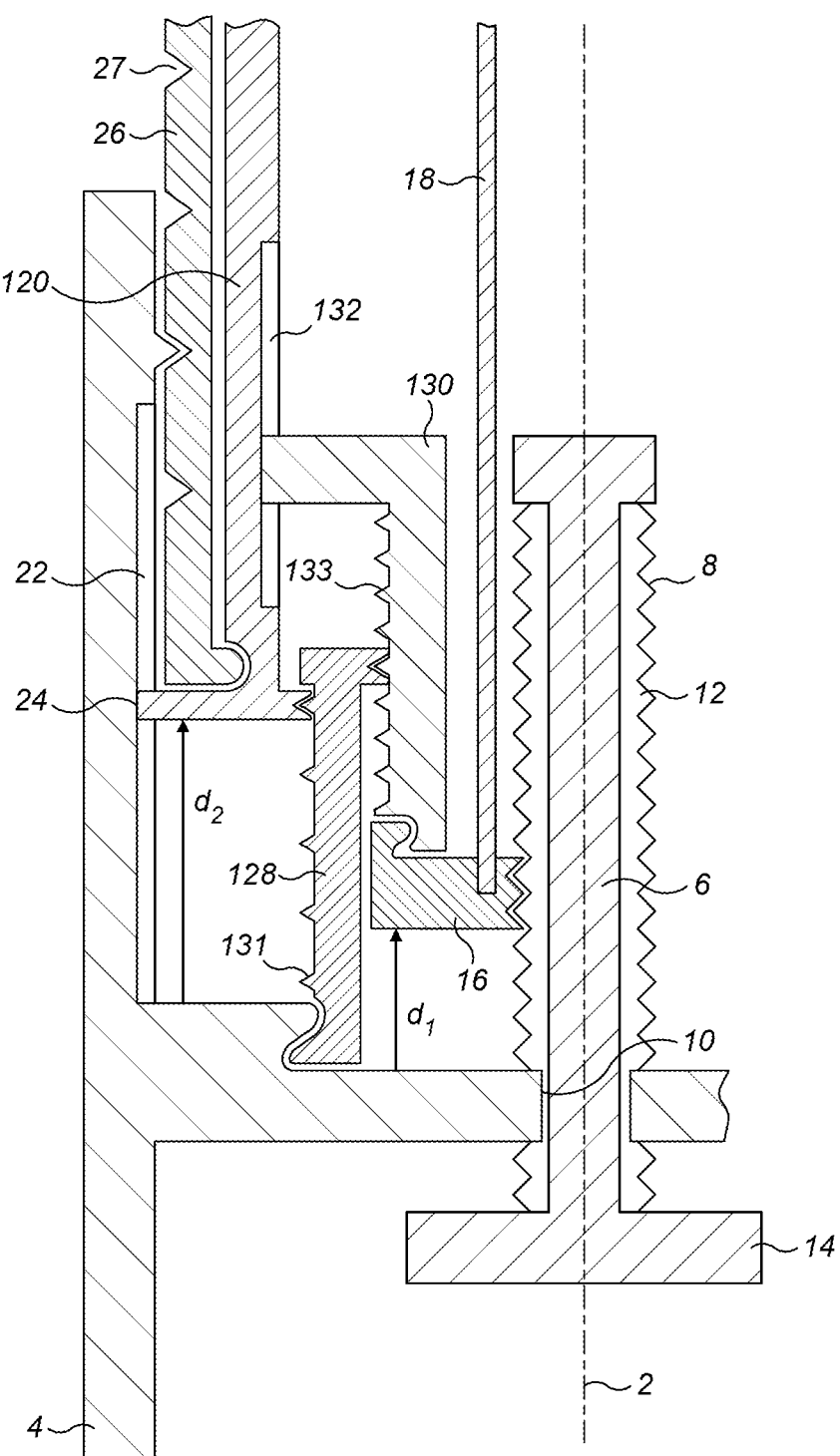
FIG. 2 is a schematic illustration of a second gearing mechanism in accordance with the present invention.
Figure 3:
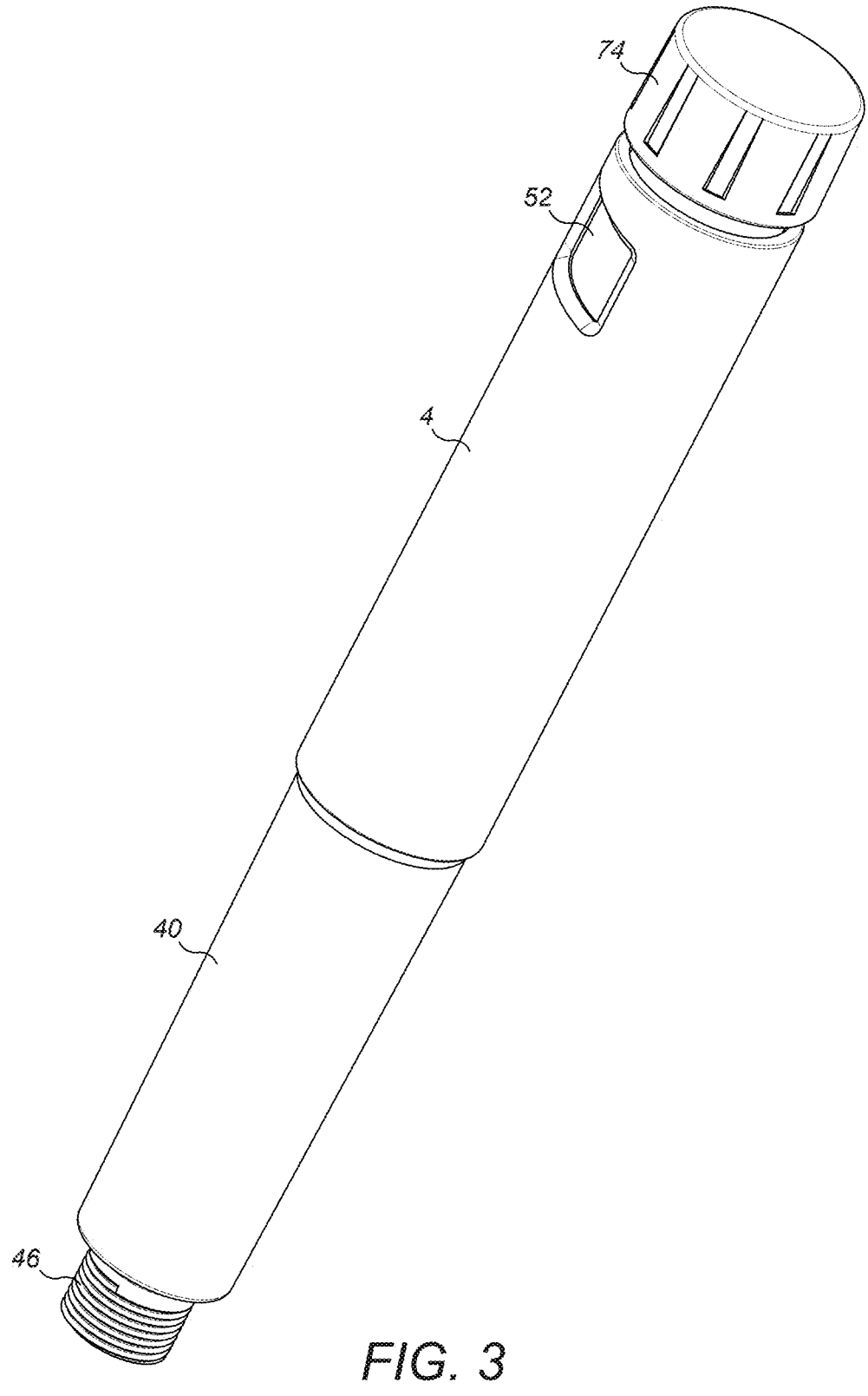
FIG. 3 is a perspective view of a dose delivery device according to the invention.
Figure 4:
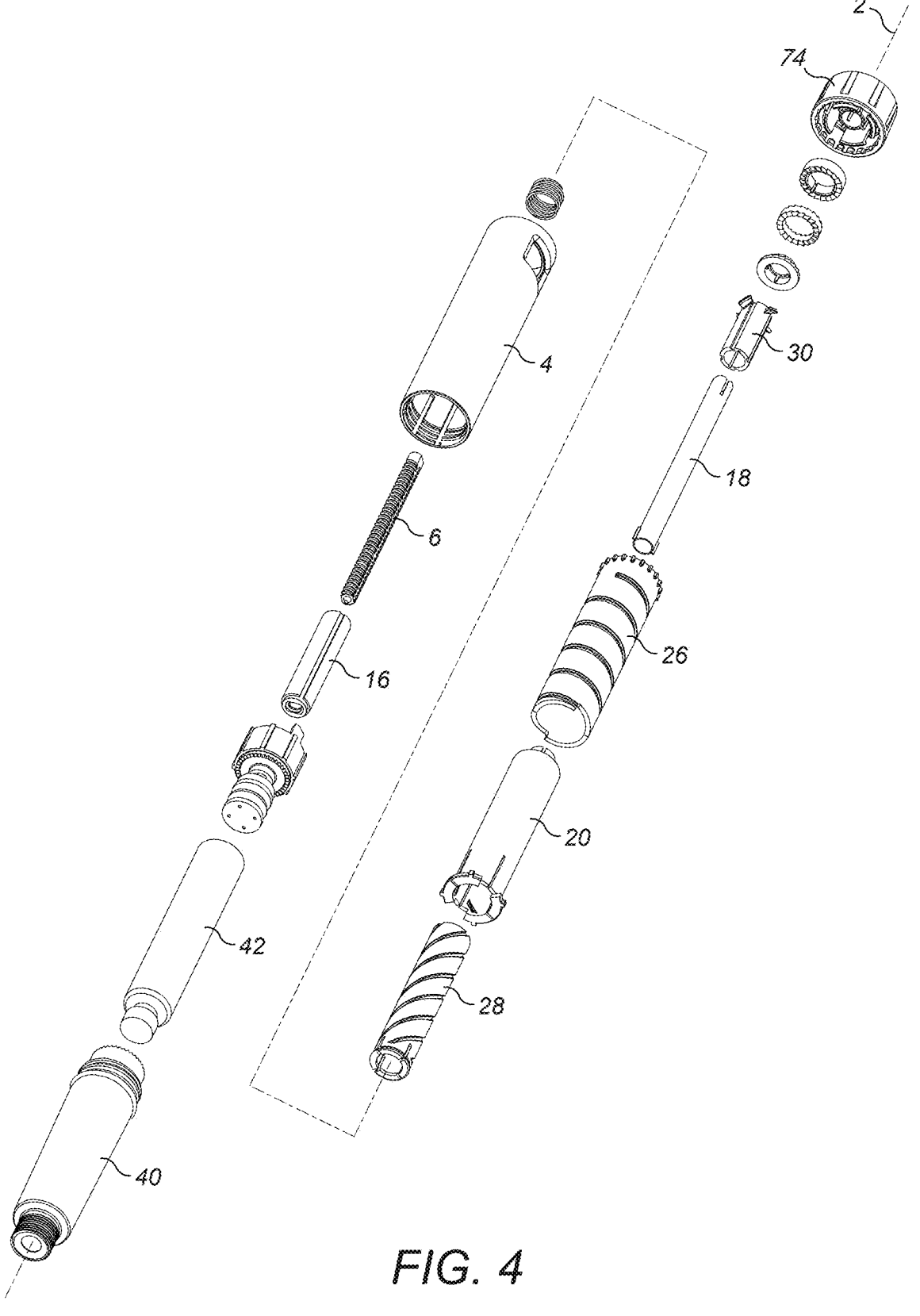
FIG. 4 is an exploded view of the dose delivery device of FIG. 3.
Figure 4A:
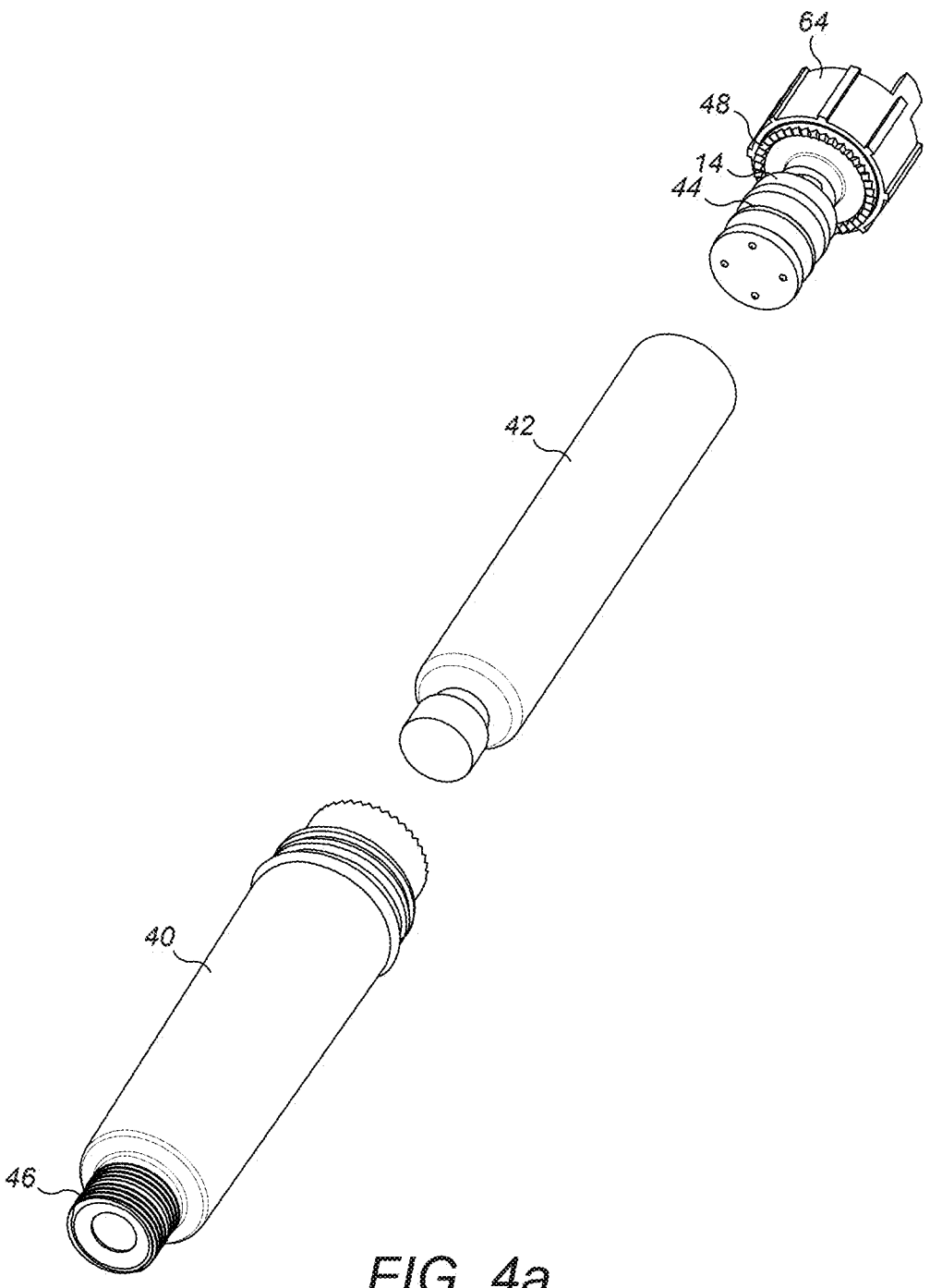
FIGS. 4a to 4d are enlargements of parts of FIG. 4.
Figure 4B:
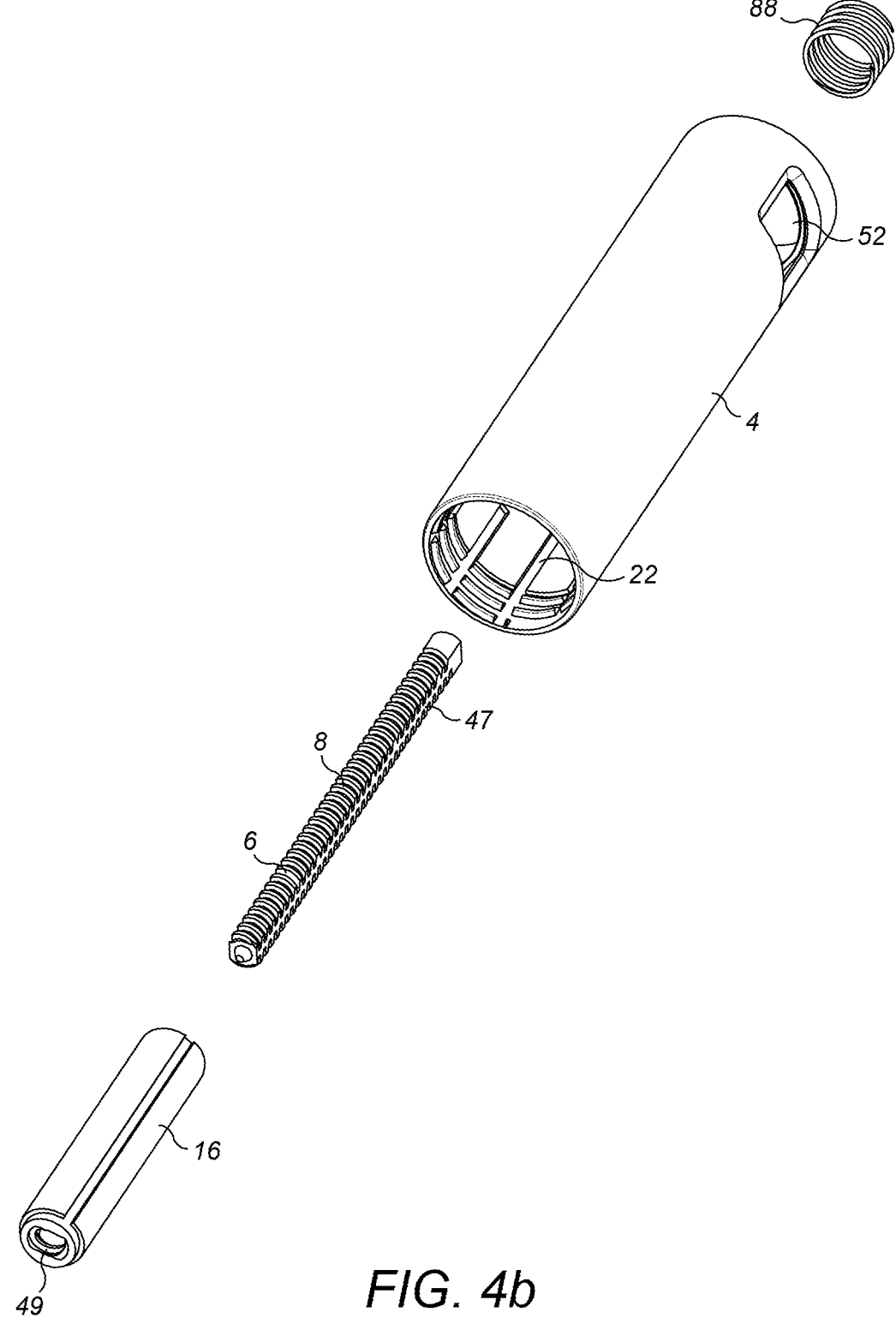
Figure 4C:
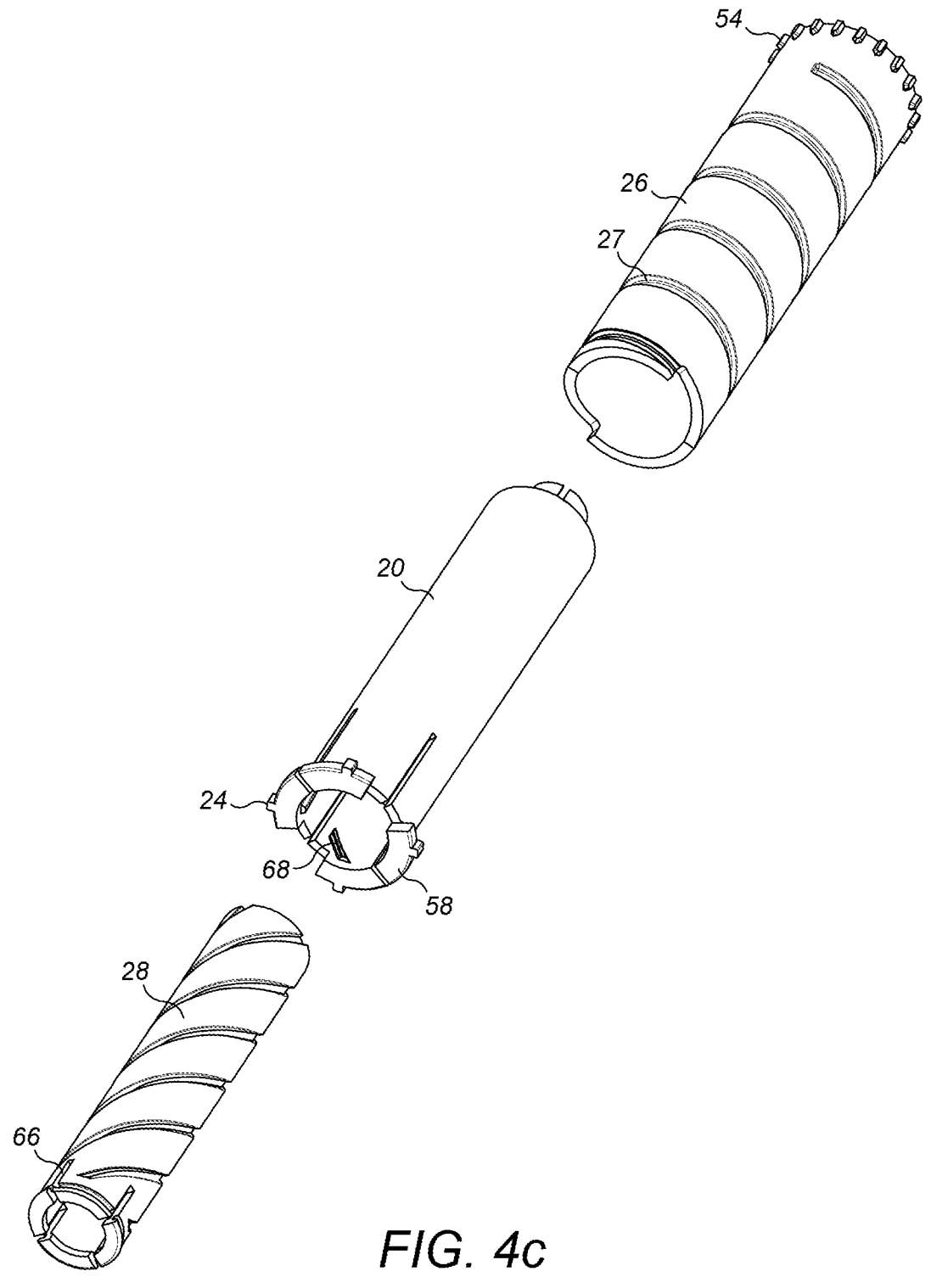
Figure 4D:
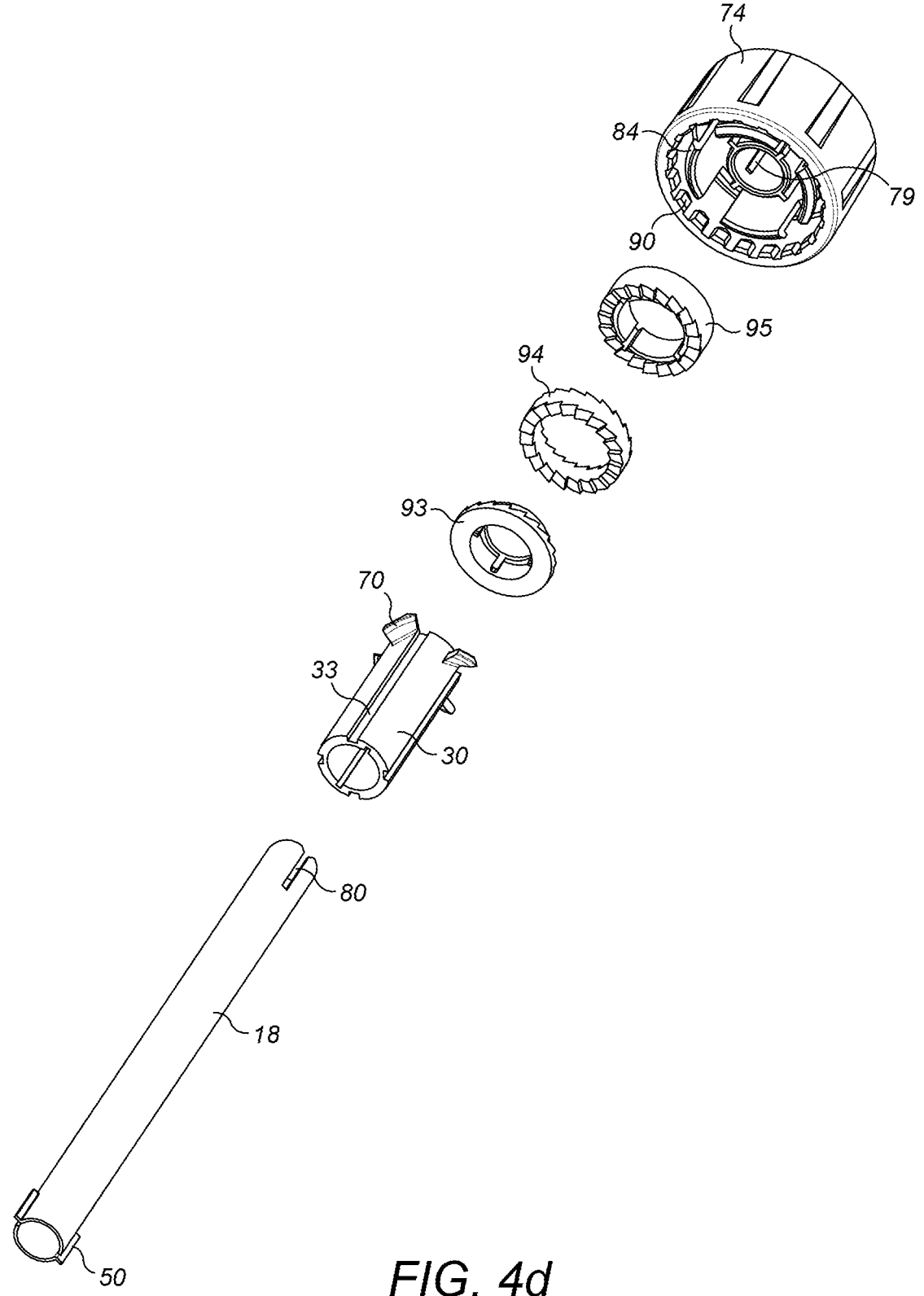

FIG. 2 illustrates an alternative gearing mechanism to that in FIG. 1. Most parts of the two mechanisms are the same so they are given the same reference numerals and their description will not be repeated here. In particular, the couplings between the connector 120 and the housing 4, between the first gear 128 and the housing 4, and between the second gear 130 and the nut 16 are the same as in FIG. 1. The differences relate to the first, second and third engagements 131,132,133 between the first gear 128, the second gear 130 and the connector 120, which are therefore given different reference numerals and will now be described.

The first gear 128 is again coupled to the connector 120 by a first engagement in the form of a first helical thread 131. However, in this mechanism, the second engagement 132 is a straight track, which permits relative axial movement but prevents relative rotation between the second gear 130 and the connector 120. On the other hand, the third engagement is a third helical thread 133 between the first and second gears 128,130. (In this mechanism there is no "second helical thread".) The third helical thread 133 has the same handedness as the first helical thread 131 but a smaller pitch.

During operation of the device of FIG. 2, the first gear 128 is prevented from moving axially, the second gear 130 moves axially with the nut 16 through the first axial distance $d_1$ and the connector 120 moves axially through the second axial distance $d_2$. The connector 120 engages the first gear 128 via the first helical thread 131 so the axial movement of the connector 120 relative to the first gear 128 causes the first gear 128 to rotate at a rate determined by the pitch of the first helical thread 131. Because the connector 120 and the second gear 130 are coupled by a straight track 132, there can be no relative rotation between the second gear 130 and the connector 120, while the straight track 132 accommodates the relative axial movement between the connector 120 and the second gear 130. The second gear 130 moves axially at a rate determined by the movement of the nut 16. The pitch of the third helical thread 133 must therefore be such that it can accommodate these simultaneous relative axial and rotational movements. In practice, the values are related by the following equation:

$$\frac{p_3}{p_1} = \frac{1}{R}$$

where:

p₁ is the pitch of the first helical thread 131,
p₃ is the pitch of the third helical thread 133, and
R is the gear ratio, $R=d_2/d_1$ The gear ratio R is also equal to the ratio between the pitch of the sleeve thread 27 and the pitch of the piston rod thread 8.

The pitches $p_1$ and $p_3$ of the first and third helical threads 131,133 may be chosen to have any suitable values, provided they are in this ratio.

In FIG. 1, the first engagement 31 is a helical thread, the second engagement 32 is a helical thread and the third engagement 33 is a straight track. In FIG. 2, the first engagement 131 is a helical thread, the second engagement 132 is a straight track and the third engagement 133 is a helical thread. In principle, all three engagements could be formed as helical threads, which would provide another degree of freedom in choosing the relative pitches of those threads. However, any benefit that may offer is likely to be outweighed by the additional complexity of the design. The first engagement cannot be formed as a straight track because then the first gear would be both axially and rotationally locked to the housing. In any given device, the second and third engagements cannot both be formed as straight tracks because then the connector, the first gear and the second gear would all be rotationally locked together and the differential axial movement between the connector and the nut 16 could not be accommodated.

In the present invention, when the engagement between two components is via a helical thread, it is generally sufficient for just one of the components to comprise a full thread and for the other component to comprise one or more short thread sections that are complementary to it. There is generally a free choice of which component should comprise the full thread and which should comprise the thread sections and there is no intention to limit the invention to the particular choices illustrated in the drawings. Similarly, when the engagement between two components is via a straight track comprising one or more projections that run in complementary channels, there is generally a free choice of which component should comprise the projections and which should comprise the channels. Again, there is no intention to limit the invention to the particular choices illustrated in the drawings. It will be understood that arrangements other than projections running in channels are possible for allowing two components to move axially without relative rotation. For example, one component may slide telescopically within the other, the two components having complementary, non-circular cross sections.

FIGS. 3 to 6 illustrate one embodiment of a dose delivery device according to the invention. This embodiment employs a gearing mechanism of the kind illustrated in FIG. 1 and the same reference numerals will be used.

A cartridge holder 40 is screwed into the front end of the housing 4. The cartridge holder 40 holds a drug cartridge 42, which in turn contains a piston 44 that can be moved forwards along the axis to displace drug from the cartridge 42. The cartridge holder 40 further comprises a thread 46 for attaching a double-ended hollow needle (not shown), of which one end can pierce a septum of the drug cartridge 42 and the other end can deliver drug displaced from the cartridge 42 into the skin of a patient.

A piston rod 6 lies along the axis 2 of the device such that a foot 14 at the front end of the piston rod engages the piston 44 to push it along the drug cartridge 42. The piston rod 6 comprises an external thread 8, which is interrupted by an opposing pair of flats to provide the piston rod 6 with a non-circular cross section.

A piston rod guide 48 is fixed in the housing 4 so that, at least while the cartridge holder 40 is attached, the piston rod guide 48 cannot move relative to the housing 4. The piston rod guide 48 defines the central aperture 10 through which the piston rod 6 can slide along the axis 2. The aperture 10 has a non-circular shape complementary to the cross section of the piston rod 6, which prevents the piston rod 6 from rotating relative to the housing 4.

The piston rod 6 passes through the bore of a nut 16, the nut 16 comprising an internal thread 49 at its forward end, which engages the external thread 8 of the piston rod 6. A rigid tube 18 extends rearwards from the nut 16 and surrounds the piston rod 6 without engaging it. The tube 18 is coupled to the nut 16 such that the tube 18 can move axially but not rotationally relative to the nut 16. Therefore, when the tube 18 is rotated the nut 16 must rotate too. In the illustrated embodiment, axial ribs 50 on the tube 18 engage internal, axial slots in the nut 16 (not visible in the drawings). Alternatively, the ribs could be provided in the nut and the slots could be provided in the tube.

A dose dial sleeve 26 is nested inside the housing 4 and comprises a helical sleeve thread 27 on its outer surface. One or more thread segments 51 on the inner wall of the housing 4 engage the sleeve thread 27 so that the dose dial sleeve 26 can move relative to the housing 4 by following the helical path of the sleeve thread 27. A window 52 is provided in the housing 4 to allow indicia on the dose dial sleeve 26 (not illustrated) to be viewed as the sleeve is rotated past the window 52 and thereby to indicate to a user the dose that has been set. The dose dial sleeve 26 comprises an array of teeth 54 disposed around the outer circumference of its rearward end. The dose dial sleeve 26 further comprises an internal flange 56 close to its rearward end.

A generally cylindrical connector 20 is located concentrically inside the dose dial sleeve 26. At its forward end, the connector 20 comprises an outer flange 58, from which a number of lugs 24 project radially outwards. In the illustrated embodiment the number of lugs 24 is four but other numbers are possible. The lugs 24 engage a corresponding number of axially aligned straight tracks 22 in the interior of the housing, whereby the connector 20 can slide axially but cannot rotate relative to the housing 4. Towards the rearward end of the connector 20, its diameter is stepped down via a shoulder 62 to form a neck 60 of reduced diameter, which is in sliding engagement with an external surface of the tube 18. The shoulder 62 of the connector 20 axially engages a front face of the inner flange 56 of the dose dial sleeve 26. A first ratchet part 93 (described below) is fixed to the neck 60 of the connector 20 and axially engages a rear face of the inner flange 56 of the dose dial sleeve 26. The dose dial sleeve 26 is thereby constrained to move axially with the connector 20 but relative rotation between them remains possible.

A first gear 28 is nested concentrically inside the connector 20 and outside the nut 16. An anchor piece 64 is fixed against axial or rotational movement inside the housing 4 and engages a forward end of the first gear 28 such that the first gear 28 is prevented from moving axially but remains free to rotate about the axis 2. The forward end of the first gear 28 is divided by a number of slots 66 to form segments with enough flexibility to snap fit into engagement with the anchor piece 64. The first gear 28 is coupled to the connector 20 by a first threaded engagement, comprising a helical thread 31 on the exterior of the first gear 28, which is engaged by thread segments 68 on the interior of the connector 20. It will be recalled that the connector 20 can only move axially and the first gear 28 can only move rotationally so the relative rate of these two movements is determined by the pitch $p_1$ of this first helical thread 31.

A second gear 30 has substantially the same diameter as the nut 16. It is positioned concentrically about the axis 2, nested between the first gear 28 and the tube 18, and offset axially to the rear of the nut 16. The nut 16 and the second gear 30 abut one another such that if the nut 16 moves rearwards, it also drives the second gear 30 rearwards, but the second gear 30 remains free to rotate relative to the nut 16. The second gear 30 is coupled to the connector 20 by a second engagement, comprising short thread segments 70 on the exterior of the second gear 30 that engage an internal helical thread 32 of the connector 20. The second gear 30 is coupled to the first gear 28 by a third engagement, comprising straight axial tracks 33 on the exterior of the second gear 30, which are engaged by inward projections 72 on the interior of the first gear 28 (seen in FIG. 5). Thereby the first and second gears 28,30 can move axially but not rotationally relative to one another. It can now be understood that the relationship between the nut 16, the first gear 28, the second gear 30 and the connector 20 is the same as the gearing mechanism previously described in relation to FIG. 1.

A dose selector 74 is provided at the rearward end of the device. A skirt 75 of the dose selector 74 provides a grip 76 on its outer surface, by which a user can turn the dose selector 74 to set a desired dose. The dose selector 74 is mounted on the rearward end of the tube 18 such that the dose selector 74 can slide a short distance axially relative to the tube 18 but there can be no relative rotation between them. In the illustrated embodiment, an internal sleeve 78 of the dose selector 74 comprises axial ribs 79, which engage axial slots 80 in the tube 18. Alternatively, the ribs could be provided on the tube and the slots could be provided in the dose selector.

The dose selector 74 is retained on the device by forwardly extending arms 82 ending in hooks 84, which snap fit behind corresponding hooks 86 at the rear end of the dose dial sleeve 26. A compression spring 88 urges the dose selector 74 rearwards until it is stopped by engagement between the respective hooks 84,86. The skirt 75 of the dose selector 74 comprises an array of teeth 90 disposed around the inner circumference of its forward end. These teeth 90 complement the external teeth 54 on the dose dial sleeve 26 so that, when the respective hooks 84,86 of the dose selector 74 and the dose dial sleeve 26 are in engagement, the respective sets of teeth 90,54 also engage each other and prevent relative rotation between the dose selector 74 and the dose dial sleeve 26.

A forward end of the compression spring 88 bears against a click mechanism in the form of a two-way rotary ratchet assembly 92, which comprises first, second and third ratchet parts 93,94,95. The first ratchet part 93 is rotationally fixed to the neck 60 of the connector 20 and the third ratchet part 95 is rotationally fixed to the dose selector 74. The second ratchet part 94 is formed as a rotary collar between the first and third ratchet parts 93,95. A first set of ratchet teeth permits relative rotation between the first and second ratchet parts 93,94 in a first angular direction but not in a second, opposite angular direction. A second set of ratchet teeth permits relative rotation between the second and third ratchet parts 94,95 in the second angular direction but not in the first angular direction. The ratchet parts 93,94,95 are maintained under axial compression by the spring 88 so that in order for the respective ratchet teeth of each set to pass one another, they must first move axially against the force of the spring 88 before rebounding with a click. The angular spacing of the ratchet teeth may be chosen such that each click corresponds to a unit added to or removed from the set dose.

The operation of the illustrated device will now be described.

Figure 5:
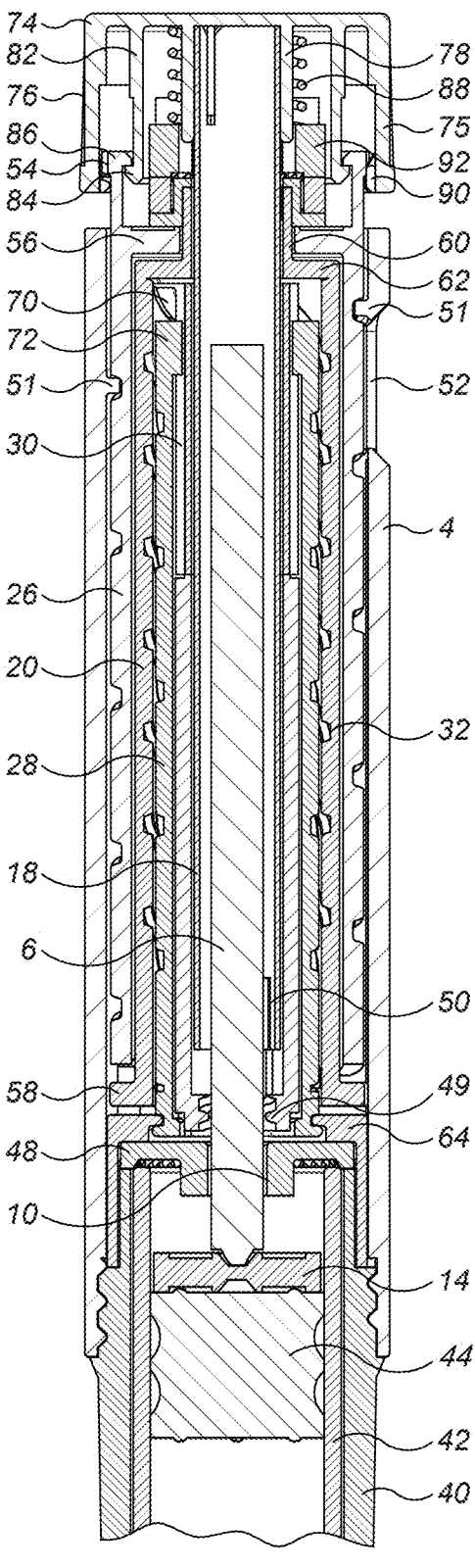
FIG. 5 is a longitudinal section of part of the dose delivery device of FIG. 3.
Figure 6:
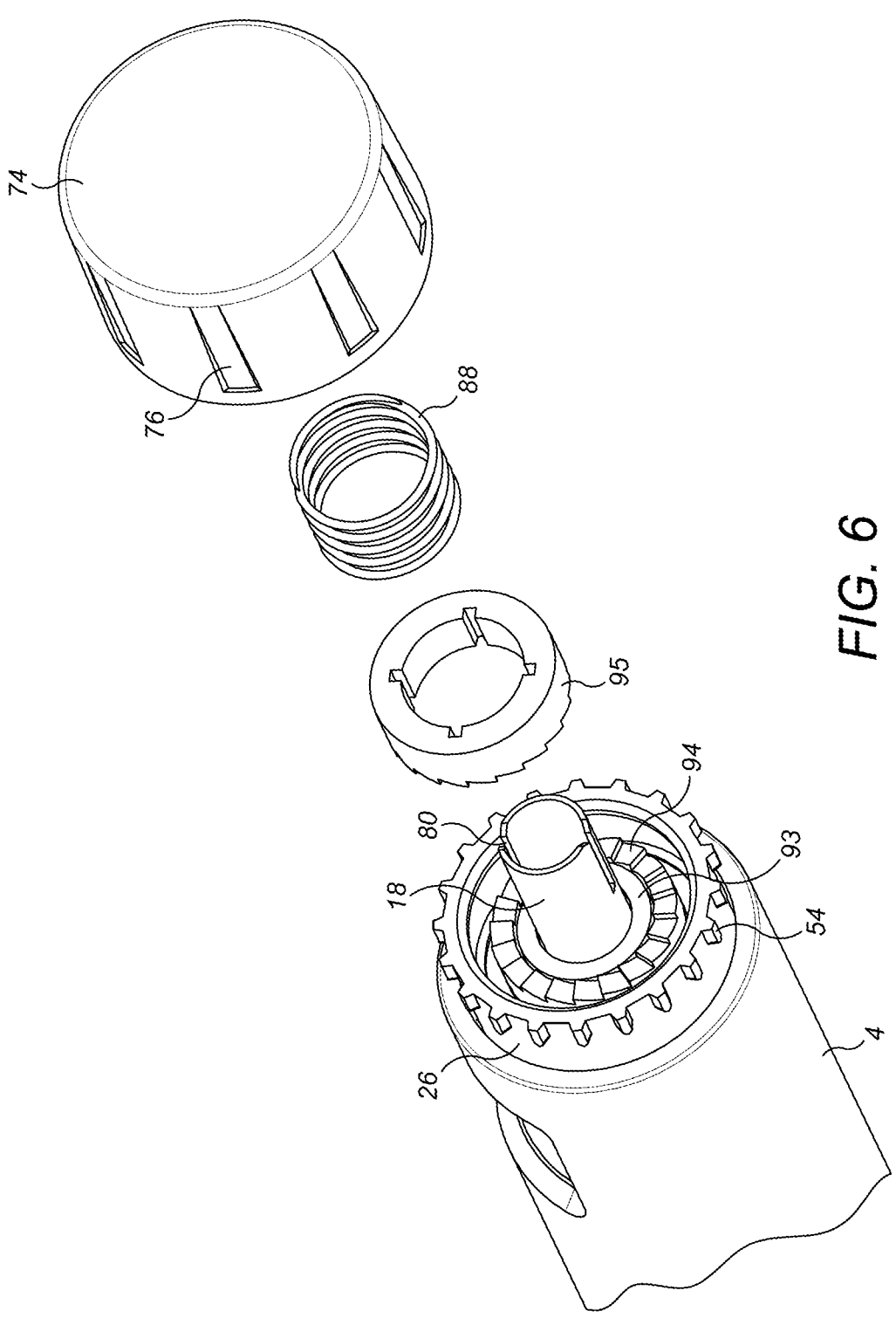
FIG. 6 is an exploded perspective view of components the dose dial mechanism of the dose delivery device of FIG. 3.

FIG. 5 shows the device in its initial configuration before a new dose (not necessarily being the first dose) is set. The nut 16, connector 20, first gear 28, second gear 30 and dose dial sleeve 26 are all positioned as far forwards as they will go and the dose dial sleeve 26 displays a set dose of zero through the window 52. In the dose setting mode of operation, the compression spring 88 is extended to push the dose selector 74 rearwards relative to the dose dial sleeve 26 until further movement is prevented by engagement of the respective hooks 84,86. The respective teeth 54,90 are thereby also engaged to lock the dose selector 74 rotationally to the dose dial sleeve. Because the dose selector 74 is displaced rearwards, the tube 18 has some freedom to move axially but it remains rotationally locked to the dose selector 74 and to the nut 16.

When the user turns the dose selector 74 in the first angular direction to increase the set dose, the dose dial sleeve 26, being rotationally locked to the dose selector 74, is rotated through the same angle and displays a succession of indicia through the window 52 to indicate the new dose that has been set. The dose dial sleeve 26 simultaneously follows the sleeve thread 27 and moves rearwards relative to the housing through an axial distance (the "second axial distance" $d_2$) determined by the pitch of the sleeve thread 27. As previously described, the connector 20 is constrained to move axially with the dose dial sleeve 26. Under the force of the compression spring 88, the hooks 84 of the dose selector 74 remain in engagement with the hooks 86 of the dose dial sleeve 26 so the dose selector 74 also follows the movement of the dose dial sleeve 26 through the same axial distance $d_2$. Meanwhile, the third ratchet part 95 rotates with the dose selector 74. The second ratchet part 94 cannot rotate in this direction relative to the first ratchet part 93, which in turn remains rotationally locked to the connector 20 and thereby to the housing. Therefore the third ratchet part 95 clicks over the second ratchet part 94 to provide further audible and tactile feedback to the user of the dose being set.

If the user has turned the dose selector 74 too far and wishes to reduce the set dose, the dose selector 74 can simply be turned in the opposite angular direction and the dose dial sleeve 26 will be screwed back into the housing 4, following the sleeve thread 27 to indicate the new, reduced dose through the window 52. When the dose selector 74 is turned in this second angular direction, the second and third ratchet parts 94,95 rotate with it, while the second ratchet part 94 clicks over the non-rotating first ratchet part 93 to provide audible and tactile feedback of the change in the set dose.

Because the dose selector 74 is rotationally locked to the rigid tube 18, which in turn is rotationally locked to the nut 16, rotation of the dose selector 74 in either direction causes the nut 16 to rotate through the same angle. The nut 16 moves along the piston rod thread 8 through an axial distance $d_1$, which is determined by the pitch of the piston rod thread 8 and which is smaller than the axial distance $d_2$ moved by the dose dial sleeve 26 and the dose selector 74. The differential axial movement is accommodated by the tube 18 sliding axially relative to the nut 16 and/or the dose selector 74.

The forward or backward axial movement of the nut 16, but not its rotational movement, is transmitted to the second gear 30. This activates the gearing mechanism previously described in relation to FIG. 1, whereby co-rotation and relative axial movement of the first and second gears 28,30 accommodates the difference between axial movement of the nut 16 and the second gear 30 through the axial distance $d_1$ compared with movement of the connector 20 through the greater axial distance $d_2$.

When the desired dose has been set, the user pushes the dose selector 74 forwards to inject the set dose. The dose selector 74 first moves axially relative to the dose dial sleeve 26, against the force of the spring 88, to disengage the respective teeth 90,54 and thereby free the dose selector 74 and dose dial sleeve 26 to rotate relative to one another. The axial movement of the dose selector 74 relative to the dose dial sleeve 26 continues until the end of the internal sleeve 78 of the dose selector 74 comes into abutment with the ratchet assembly 92 or until the spring 88 is fully compressed. The respective ratchet parts 93,94,95 are thereby prevented from moving axially so they cannot click past one another and the dose selector 74 is prevented from rotating relative to the connector 20. The device is now in dose delivery mode.

Further force applied to the dose selector 74 is transmitted directly through the ratchet assembly 92 (without any rotation) to the neck 60 of the connector 20 and causes the connector 20 to slide axially forwards to return to its initial position. The gearing mechanism now works in reverse, whereby the forward axial movement of the connector 20 through distance $d_2$ is converted, via the first gear 28, into forward axial movement of the second gear 30 through distance $d_1$. The second gear 30 pushes the nut 16 forwards through the same distance to return to its initial axial position. The piston rod thread 8 may be self-locking so that applying an axial force to the nut 16 does not cause it to rotate along the thread 8. In any case, the nut 16 remains rotationally locked via the tube 18 to the dose selector 74, which is not rotating in this dose delivery mode. Therefore the nut 16 moves forwards without rotation and it also drives the piston rod 6 forwards without rotation through the axial distance $d_1$, which is proportional to the set dose.

The axial force applied to the dose selector 74 is also transmitted through the first ratchet part 93 to the inner flange 56 of the dose dial sleeve 26. This drives the dose dial sleeve 26 to move forwards, which it can do by simultaneously rotating to follow the sleeve thread 27 until it returns to its initial position, defined by a rotary stop in the sleeve thread 27.

Once the dose has been delivered and the nut 16, connector 20 and dose dial sleeve 26 have returned to their initial axial positions, pressure on the dose selector 74 may be released. The compression spring 88 then returns the dose selector 74 to its initial position seen in FIG. 5. The device may now be used to set and deliver further doses until the supply of drug in the cartridge 42 is exhausted.

The described device may be changed in various ways without departing from the present invention. For example, instead of the illustrated two-way ratchet 92, an alternative click mechanism may comprise two mutually facing rings of symmetrical triangular teeth, which can move against the force of the spring 88 to click past one another when the dose selector 74 is rotated in either direction during the dose setting mode. During the dose delivery mode, the spring 88 is compressed and the teeth are clamped together to prevent relative rotation between the dose selector 74 and the connector 20.

Means may be provided to prevent a greater dose being set than the amount of drug remaining in the cartridge 42. For example, the piston rod 6 may be provided with a head such that the axial distance between the piston rod head and the initial position of the nut thread 49 is a measure of the remaining drug. Then, as the amount of drug remaining approaches zero, the axial distance between the piston rod head and initial position of the nut thread 49 will also approach zero. During a subsequent dose setting mode, the head will prevent the nut 16 being retracted far enough to set a dose that is greater than the amount of drug remaining.

If the device is intended to be reusable, so that an empty drug cartridge 42 may be replaced by a full one, a reset mechanism may also be provided to facilitate returning the piston rod 6 to its initial position. For example, the reset mechanism may permit the piston rod guide 48 to be rotationally disengaged from the housing 4 when the cartridge holder 40 is removed so that the piston rod 6 can be rotated relative to the nut 16 and thereby be screwed back along the piston rod thread 8 to return to its required position prior to delivery of a first dose from the replacement cartridge.

The invention claimed is:

1. A dose delivery device, comprising:
a housing;
a piston rod configured to move axially without rotation relative to the housing, the piston rod comprising a piston rod thread;
a nut engaging the piston rod thread;
a dose selector rotationally locked to the nut;
a connector configured to move axially without rotation relative to the housing;
a first gear configured to rotate without axial movement relative to the housing, the first gear being coupled to the connector by a first engagement, the first engagement being a first helical thread; and
a second gear coupled to the nut so as to permit relative rotation but not relative axial movement between the second gear and the nut, the second gear being coupled to the connector by a second engagement and to the first gear by a third engagement.

2. A dose delivery device according to claim 1, wherein the second engagement is a straight track, which permits relative axial movement but prevents relative rotation between the second gear and the connector.

3. A dose delivery device according to claim 2, wherein:
the third engagement is a third helical thread;
the first and third helical threads are of the same handedness; and
the third helical thread has a smaller pitch than the first helical thread.

4. A dose delivery device according to claim 1, further comprising a dose dial sleeve configured to rotate without axial movement relative to the connector, the dose dial sleeve engaging the housing via a sleeve thread.

5. A dose delivery device according to claim 4, wherein the dose selector is axially movable relative to the dose dial sleeve, such that:
in a dose setting mode, the dose selector is rotationally locked to the dose dial sleeve but is rotationally disengaged from the connector; and
in a dose delivery mode, the dose selector is rotationally disengaged from the dose dial sleeve.

6. A dose delivery device according to claim 5, further comprising a click mechanism that acts between the dose selector and the connector to generate clicks as the dose selector rotates relative to the connector in the dose setting mode; and to lock the dose selector rotationally to the connector in the dose delivery mode.

7. A dose delivery device according to claim 1, wherein the nut and the connector are configured such that, when the nut is rotated the nut moves along the piston rod thread through a first axial distance, and the connector moves in the same direction through a second axial distance that is greater than the first axial distance.

8. A dose delivery device comprising:
a housing;
a piston rod configured to move axially without rotation relative to the housing, the piston rod comprising a piston rod thread;
a nut engaging the piston rod thread;
a dose selector rotationally locked to the nut;
a connector configured to move axially without rotation relative to the housing;
a first gear configured to rotate without axial movement relative to the housing, the first gear being coupled to the connector by a first engagement, the first engagement being a first helical thread; and
a second gear coupled to the nut so as to permit relative rotation but not relative axial movement between the second gear and the nut, the second gear being coupled to the connector by a second engagement and to the first gear by a third engagement,
wherein the third engagement is a straight track, which permits relative axial movement but prevents relative rotation between the first and second gears.

9. A dose delivery device according to claim 8, wherein:
the second engagement is a second helical thread;
the first and second helical threads are of the same handedness; and
the second helical thread has a smaller pitch than the first helical thread.

10. A method of operating a dose delivery device, which comprises a housing and a piston rod configured to move axially without rotation relative to the housing; the method comprising:
in a dose setting mode, rotating a dose selector relative to the housing, the dose selector being rotationally locked to a nut, which thereby moves in a backward direction along a thread of the piston rod through a first axial distance; and
transmitting the axial movement of the nut through a gearing mechanism to a connector that is configured to move axially without rotation relative to the housing, such that the connector moves in the backward direction from an initial position through a second axial distance greater than the first axial distance;
wherein the gearing mechanism comprises:
a first gear that rotates without axial movement relative to the housing, the first gear being coupled to the connector by a first engagement, the first engagement being a first helical thread; and
a second gear coupled to the nut so as to permit relative rotation but not relative axial movement between the second gear and the nut, the second gear being coupled to the connector by a second engagement and to the first gear by a third engagement.

11. A method according to claim 10, wherein the dose selector is coupled to the connector such that the dose selector also moves through the second axial distance.

12. A method according to claim 10, further comprising, in a dose delivery mode:
pushing the connector in a forward direction through the second axial distance to the initial position; and
transmitting the axial movement of the connector through the gearing mechanism, such that the nut and the piston rod move in the forward direction through the first axial distance.

13. A method according to claim 12 wherein a dose dial sleeve also moves through the second axial distance, while rotating to follow a sleeve thread between the dose dial sleeve and the housing.

14. A method according to claim 13, wherein:
in the dose setting mode, the dose selector is rotationally locked to the dose dial sleeve; and
in the dose delivery mode, the dose selector is rotationally disengaged from the dose dial sleeve.

* * * * *